US007235602B2

(12) United States Patent
Klettke et al.

(10) Patent No.: US 7,235,602 B2
(45) Date of Patent: Jun. 26, 2007

(54) POLYMERIZABLE PREPARATIONS ON THE BASIS OF SILICON COMPOUNDS COMPRISING ALIPHATIC AND CYCLOALIPHATIC EPOXIDE GROUPS

(75) Inventors: Thomas Klettke, Diessen (DE); Karsten Dede, Landsberg (DE)

(73) Assignee: 3M ESPE AG, Seefeld (DE)

( * ) Notice: Subject to any disclaimer, the term of this patent is extended or adjusted under 35 U.S.C. 154(b) by 129 days.

(21) Appl. No.: 10/468,532

(22) PCT Filed: Feb. 13, 2002

(86) PCT No.: PCT/EP02/01491

§ 371 (c)(1),
(2), (4) Date: Dec. 18, 2003

(87) PCT Pub. No.: WO02/066535

PCT Pub. Date: Aug. 29, 2002

(65) Prior Publication Data

US 2004/0186202 A1   Sep. 23, 2004

(30) Foreign Application Priority Data

Feb. 19, 2001   (DE) ................................ 101 07 985

(51) Int. Cl.
*C08L 83/06* (2006.01)
(52) U.S. Cl. ...................... 524/858; 523/403; 523/406; 427/386; 427/387
(58) Field of Classification Search ................ 523/403, 523/406; 524/858
See application file for complete search history.

(56) References Cited

U.S. PATENT DOCUMENTS

| 900,506 | A | 10/1908 | Forbes |
| 907,149 | A | 12/1908 | Hookham et al. |
| 2,716,123 | A | 8/1955 | Frostick, Jr. et al. |
| 2,745,847 | A | 5/1956 | Phillips et al. |
| 2,750,395 | A | 6/1956 | Phillips et al. |
| 2,863,881 | A | 12/1958 | Phillips et al. |
| 2,948,668 | A | 8/1960 | Bender et al. |
| 2,985,667 | A | 5/1961 | Tinsley et al. |
| 3,066,112 | A | 11/1962 | Bowen |
| 3,187,018 | A | 6/1965 | Tinsley et al. |
| 4,172,951 | A | 10/1979 | Gruber et al. |
| 4,767,798 | A | 8/1988 | Gasser et al. |
| 4,843,136 | A | 6/1989 | Reiners et al. |
| 4,902,368 | A | 2/1990 | Oldham |
| 5,484,950 | A | 1/1996 | Crivello |
| 5,556,896 | A | 9/1996 | Byerley et al. |
| 5,639,413 | A | 6/1997 | Crivello |
| 5,808,108 | A | * 9/1998 | Chappelow et al. ........ 549/335 |
| 5,824,720 | A | 10/1998 | Nowak et al. |
| 6,084,004 | A | 7/2000 | Weinmann et al. |
| 6,245,828 | B1 | 6/2001 | Weinmann et al. |

FOREIGN PATENT DOCUMENTS

| DE | 27 14 538 A1 | 10/1978 |
| DE | 28 16 823 A1 | 10/1978 |
| DE | 43 40 949 A1 | 9/1995 |
| DE | 44 45 266 A1 | 6/1996 |
| DE | 196 48 283 A1 | 5/1998 |
| EP | 0 238 025 A2 | 9/1987 |
| EP | 0 261 520 A2 | 6/1988 |
| EP | 0 412 420 A2 | 2/1991 |
| EP | 0 449 027 A2 | 10/1991 |
| EP | 0 238 025 B1 | 12/1992 |
| EP | 0 261 520 B1 | 12/1992 |
| EP | 0 412 420 B1 | 3/1994 |
| EP | 0 661 324 A2 | 7/1995 |
| EP | 0 897 710 A2 | 2/1999 |
| EP | 0 661 324 B1 | 7/2000 |
| GB | 1 123 960 | 8/1968 |
| GB | 1 576 080 | 4/1978 |
| WO | WO 95/25139 A1 | 9/1995 |
| WO | WO 95/30402 A1 | 11/1995 |
| WO | WO 96/30182 A1 | 10/1996 |
| WO | WO 98/22521 A1 | 5/1998 |
| WO | WO 98/33645 A1 | 8/1998 |
| WO | WO 98/47046 A1 | 10/1998 |
| WO | WO 98/47047 A1 | 10/1998 |
| WO | WO 00/19967 A1 | 4/2000 |

OTHER PUBLICATIONS

Lee et al., Hand Book of Epoxy Resins, McGraw-Hill Book Co. (1967), pp. 13-1 to 13-22 and 14-1 to 14-53.*
Crivello et al., "Regioselective Hydrosilations. I. The Hydrosilation of α,ω-Dihydrogen Functional Oligopolydimethylsiloxanes with 3-Vinyl-7-oxabicyclo [4.1.0]heptane," *Journal of Polymer Science, Part A: Polymer Chemistry*, vol. 31, Title page (1 pg), Publication pages (2 pgs), and pp. 2563-2572 (1993).
Crivello et al., "Regioselective Hydrosilations. II. The Synthesis of Silicon-Hydrogen Functional Compounds," *Journal of Polymer Science, Part A: Polymer Chemistry*, vol. 31, Title page (1 pg), Publication pages (2 pgs), and pp. 2729-2737 (1993).

(Continued)

*Primary Examiner*—Kuo-Liang Peng
(74) *Attorney, Agent, or Firm*—Mueting, Raasch & Gebhardt, P.A.

(57) ABSTRACT

The invention relates to polymerizable preparations that contain: (a) 1 to 80% by weight of an epoxide or of a mixture of epoxides of the general formula (I), wherein n and m independently are 1, 2, 3, or 4, and wherein the molar mass of the epoxide or the average molar mass of the mixture of epoxides is 360 to 3000 g/mole, (b) 0 to 80% by weight of an epoxide or of a mixture of epoxides that are different from (a), (c) 3 to 85% by weight of fillers, (d) 0.01 to 25% by weight of initiators, retarders and/or accelerators, (e) 0 to 25% by weight of adjuvants, the percentages relating to the overall weight of the individual preparation.

33 Claims, No Drawings

OTHER PUBLICATIONS

Crivello et al., "Regioselective Hydrosilations. III. The Synthesis and Polymerization of Ambifunctional Silicon-Containing Epoxy Monomers," *Journal of Polymer Science, Part A: Polymer Chemistry*, vol. 31, Title page (1 pg), Publication pages (2 pgs), and pp. 3109-3119 (1993).

Crivello et al., "Regioselective Hydrosilations. IV. The Synthesis and Polymerization of Monomers Containing Epoxy and Alkoxysilane Groups," *Journal of Polymer Science, Part A: Polymer Chemistry*, vo.. 31, Title page (1 pg), Publication pages (2 pgs), and pp. 3121-3132 (1993).

Crivello et al., "The Synthesis and Study of the Photoinitiated Cationic Polymerization and Novel Cycloaliphatic Epoxides," *Journal of Polymer Science, Part A: Polymer Chemistry*, vol. 33, Title page (1 pg), Publication pages (2 pgs), and pp. 2463-2471 (1995).

Crivello et al., "The Synthesis, Characterization, and Photoinitiated Cationic Polymerization of Silicon-Containing Epoxy Resins," *Journal of Polymer Science, Part A: Polymer Chemistry*, vol. 28, Title page (1 pg), Publication pages (2 pgs), and pp. 479-503 (1990).

International Standard, ISO 4049, "Dentistry—Polymer-based filling, restorative and luting materials," Title page, Publication page, Table of Contents, Forward page, Introduction page, and pp. 1-27 (34 pp. total) (Jul. 15, 2000).

\* cited by examiner

POLYMERIZABLE PREPARATIONS ON THE BASIS OF SILICON COMPOUNDS COMPRISING ALIPHATIC AND CYCLOALIPHATIC EPOXIDE GROUPS

The present application is a U.S. National Stage Application of PCT/EP02/01491, filed 13 Feb. 2002. The application also claims the benefit under 35 U.S.C. §119 of foreign application no. DE 101 07 985.0, filed 19 Feb. 2001.

The invention relates to polymerizable preparations based on silicon-comprising epoxides and to their use.

Use has hitherto been made, in polymerizable dental materials, of mainly methacrylate and acrylate monomers. 2,2-Bis[4,1-phenylenoxy(2-hydroxy-3,1-propanediyl)methacrylic acid ester]propylidene (Bis-GMA), described by Bowen (U.S. Pat. No. 3,066,112), deserves particular attention. Mixtures of this methacrylate with triethylene glycol dimethacrylate are also still used today as monomer matrix for dental plastic direct filling materials. Methacrylic derivatives of the diformylated bis(hydroxymethyl)tri-cyclo [5.2.1.0$^{2,6}$]decane have also proved worthwhile as monomers for dental composites (W. Gruber et al., DE-A-27 14 538; W. Schmitt et al., DE-C-28 16 823; J. Reiners et al., EP-A-0 261 520). A great disadvantage of the known polymerizable dental materials is the polymerization shrinkage, which in the application as filling material, for example, can give rise to secondary caries through the formation of marginal leakage. In addition, the inhibition of polymerization by oxygen leads, in the case of dental materials based on acrylate, to the formation of a "smear layer", which, for example in fillings, is undesirable or even harmful.

Although there exists extensive experience with epoxides and cycloaliphatic epoxides (U.S. Pat. Nos. 2,716,123, 2,750,395, 2,863,881, 3,187,018), such monomers and cationically polymerizable materials formulated therefrom, with the properties necessary for dental applications, have at no time been available commercially.

The preparation of bifunctional cycloaliphatic epoxides has already been known for some time (U.S. Pat. Nos. 2,750,395, 900,506, 907,149, 2,745,847, 2,853,499, 3,187,018, 2,863,881, 2,853,498). Silicon-comprising cycloaliphatic epoxides for the preparation of three-dimensional objects by means of stereolithography have been disclosed by Crivello et al. in various publications (WO 96/30182, EP-A-0 449 027; J. Polym. Sci., Part A: Polym. Chem., 28 (1990), 479; ibid., 31 (1993), 2563; ibid., 31, (1993), 2729; ibid., 31 (1993), 3109; ibid., 31 (1993), 3121; ibid., 33 (1995) 2463).

Silicon-comprising epoxides comprising aromatic compounds have been disclosed as monomers for the preparation of vibration-damping surfaces (U.S. Pat. No. 4,902 368).

EP 412 420 A1, WO 95/25139 and GB 1 123 960 likewise disclose silicon-comprising epoxides.

A process for the preparation of silicone materials comprising an aliphatic and a cycloaliphatic epoxy functional group has been disclosed by Crivello et al. (J. Polym. Sci.: Part A, 1993, 3109-31119, and U.S. Pat. No. 5,484,950).

Cationically curable epoxide materials for dental applications are known, e.g. from U.S. Pat. No. 5,556,896. This document discloses epoxide-comprising materials which necessarily have to comprise spiroorthocarbonates as shrinkage-compensating monomers.

Furthermore, WO 95/30402 discloses photopolymerizable compounds comprising epoxide monomers. The materials disclosed in this document are unsuitable for dental applications in the oral environment because of their high water uptake in the polymerized state.

The cycloaliphatic epoxides disclosed in DE-A-4 340 949 are essentially low-molecular-weight monomers which admittedly have a reduced polymerization shrinkage but, because of their toxicological properties, do not meet the requirements of materials for dental applications.

The documents WO 98/47046, WO 98/47047 and EP-A-0 897 710 disclose epoxide materials for dental applications which are distinguished by a novel initiator system but are based on conventional epoxide monomers.

WO 98/22521 discloses polymerizable materials based on epoxides, inter alia also for dental application. The relatively high viscosity and the moderate reactivity of the monomer-comprising materials are disadvantageous to the epoxide materials revealed therein.

It is also known to a person skilled in the art that cycloaliphatic epoxide monomers, such as cyclohexene oxide derivatives, in comparison with the aliphatic epoxide monomers, exhibit an enhanced reactivity because of the higher ring strain. Cycloaliphatic derivatives are accordingly preferred for processing to polymerizable materials, if a high degree of polymerization is supposed to be achieved.

It is an object of the present invention to make available preparations which are distinguished by good handling properties, good processability, by low volume shrinkage and high reactivity in polymerization, and by high stability in the oral environment in the polymerized state. For this, the monomers should exhibit a low viscosity with simultaneously good mechanical values of the preparations comprising these monomers. Furthermore, the preparations should exhibit a satisfactory storage stability for dental applications.

This object is achieved according to the invention through polymerizable preparations comprising (a) 1 to 80 weight % of an epoxide or a mixture of epoxides of the general formula:

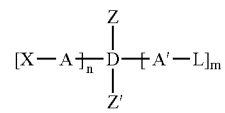

in which

A and A' represent, independently of one another, an, unbranched or branched aliphatic, cycloaliphatic or aromatic residue or a combination of these residues with 0 to 16 carbon atoms, in which one or more carbon atoms can be replaced by O, O(C=O), C=O, Si, N or S, X represents an unbranched or branched aliphatic or aromatic residue or a combination of these residues with 3 to 16 carbon atoms, in which one or more carbon atoms can be replaced by O, O(C=O), (C=O), Si, N or S and an aliphatic terminal or centrally located epoxide group is present, L represents an unbranched or branched aliphatic, cycloaliphatic or aromatic residue or a combination of these residues with 6 to 30 carbon atoms, in which one or more carbon atoms can be replaced by O, O(C=O), (C=O), Si, N or S and a cycloaliphatic epoxide group is present, Z and Z' represent, independently of one another, H or an unbranched or branched aliphatic, cycloaliphatic or aromatic residue or a combination of these residues with 0 to 10 carbon atoms, in which one or more carbon atoms can be replaced by O, O(C=O), (C=O), Si, N or S, D represents an unbranched or branched aliphatic, cycloaliphatic or aromatic residue or a combination of these residues with 1 to 55 carbon atoms, in which at least one carbon atom is replaced by SiGG', SiG or Si and one or more carbon atoms can be replaced by O, O(C=O), (C=O), N or S, G and G' represent, independently of one another, an unbranched or branched aliphatic, cycloaliphatic or aromatic residue or a combination of these residues with 1 to 15 carbon atoms, in which one or more carbon atoms can be replaced by O, O(C=O), (C=O), Si, N or S, n and m represent, independently of one another, 1, 2, 3 or 4, and in which the molar mass of the epoxide or the average molar mass of the mixture of epoxides is 360 to 3000 g/mol, (b) 0 to 80 weight % of an epoxide or a mixture of epoxides which are different from (a), (c) 3 to 85 weight % of fillers, (d) 0.01 to 25 weight % of initiators, retarders and/or accelerators, (e) 0 to 25 weight % of auxiliaries, in which the percentages are in each case with reference to the total weight of the preparation.

The preparations according to the invention with the combination of aliphatic and cyclo aliphatic epoxide groups with an average molar mass of the polymerizable compound of 200 to 3000 g/mol surprisingly also show, at a consistency convenient for the processing, a very low adhesiveness with good mechanical properties of the polymerized preparation.

Preferred polymerizable preparations comprise (a) 3 to 50 weight % of an epoxide or a mixture of epoxides of the general formula:

in which

A and A' represent, independently of one another, an unbranched or branched aliphatic, cycloaliphatic or aromatic residue or a combination of these residues with 0 to 12 carbon atoms, in which one or more carbon atoms can be replaced by O, O(C=O), C=O, Si, N or S, X represents an unbranched or branched aliphatic or aromatic residue or a combination of these residues with 3 to 14 carbon atoms, in which one or more carbon atoms can be replaced by O, O(C=O), (C=O), Si, N or S and an aliphatic terminal or centrally located epoxide group is present, L represents an unbranched or branched aliphatic, cycloaliphatic or aromatic residue or a combination of these residues with 6 to 20 carbon atoms, in which one or more carbon atoms can be replaced by O, O(C=O), (C=O), Si, N or S and a cycloaliphatic epoxide group is present, Z and Z' represent, independently of one another, H or an unbranched or branched aliphatic, cycloaliphatic or aromatic residue or a combination of these residues with 0 to 10 carbon atoms, in which one or more carbon atoms can be replaced by O, O(C=O), (C=O) or Si, D represents an unbranched or branched aliphatic, cycloaliphatic or aromatic residue or a combination of these residues with 1 to 50 carbon atoms, in which at least one carbon atom is replaced by SiGG', SiG or Si and one or more carbon atoms can be replaced by O, O(C=O) or (C=O), G and G' represent, independently of one another, an unbranched or branched aliphatic, cycloaliphatic or aromatic residue or a combination of these residues with 1 to 8 carbon atoms, in which one or more carbon atoms can be replaced by O, O(C=O), (C=O) or Si, n and m represent, independently of one another, 1, 2, 3 or 4, in which the molar mass of the epoxide or the average molar mass of the mixture of epoxides is 360 to 2500 g/mol, (b) 0 to 60 weight % of an epoxide or a mixture of epoxides which are different from (a), (c) 15 to 85 weight % of fillers, (d) 0.01 to 20 weight % of initiators, retarders and/or accelerators, (e) 0 to 25 weight % of auxiliaries, in which the percentages are in each case with reference to the total weight of the preparation.

Preparations in which the component (a) exhibits a molar mass of the epoxide or an average molar mass of the mixture of epoxides of 360 to 2500 g/mol are particularly preferred.

It is possible from this to additionally achieve, with the preparations according to the invention with the combination of aliphatic and cycloaliphatic epoxide groups with an average molar mass of the polymerizable compound of 360 to 2500 g/mol, a higher filler loading with convenient processability and consistency with retention of the low adhesiveness.

Suitable preparations can in particular comprise, as component (a), one or more epoxides of the following formula

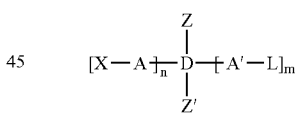

in which

A and A' represent, independently of one another, an unbranched or branched aliphatic, cycloaliphatic or aromatic residue or a combination of these residues with 0 to 12 carbon atoms, in which one or more carbon atoms can be replaced by O, O(C=O), C=O, Si, N or S, X represents an unbranched or branched aliphatic residue or a combination of these residues with 3 to 14 carbon atoms, in which one or more carbon atoms can be replaced by O, O(C=O), (C=O), Si, N or S and at least one terminal aliphatic epoxide group is present, L represents an unbranched or branched aliphatic or cycloaliphatic residue or a combination of these residues with 7 to 15 carbon atoms, in which one or more carbon atoms can be replaced by O, O(C=O), (C=O), Si, N or S, and a cycloaliphatic epoxide group of the following formula is present,

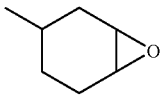

D represents an unbranched or branched aliphatic, cycloaliphatic or aromatic residue or a combination of these residues with 1 to 50 carbon atoms, in which at least one carbon atom is replaced by SiGG', SiG or Si and one or more carbon atoms can be replaced by O, O(C=O) or (C=O), G and G' represent, independently of one another, an unbranched or branched aliphatic or aromatic residue or a combination of these residues with 1 to 8 carbon atoms, in which one or more carbon atoms can be replaced by O, O(C=O), (C=O) or Si, n and m represent, independently of one another, 1, 2, 3 or 4, in which the molar mass of the epoxide or the average molar mass of the mixture of epoxides is 360 to 2500 g/mol.

It was surprisingly established that the polymerizable preparation according to the invention then exhibits particularly good handling properties if it comprises, as component (a), one or more epoxides corresponding to the following formula:

in which

A and A' represent, independently of one another, an unbranched or branched aliphatic, cycloaliphatic or aromatic [lacuna] or a combination of these residues residue with 0 to 10 carbon atoms, in which one or more carbon atoms can be replaced by O, O(C=O), C=O or Si, X represents a branched or unbranched aliphatic residue with 3 to 14 carbon atoms, in which one or more carbon atoms can be replaced by O, O(C=O), (C=O) or Si and at least one terminal aliphatic epoxide group is present, L represents an unbranched or branched aliphatic or cycloaliphatic residue or a combination of these residues with 7 to 15 carbon atoms, in which one or more carbon atoms can be replaced by O, O(C=O), (C=O) or Si and a cycloaliphatic epoxide group of the following formula is present,

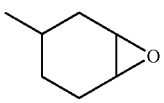

D represents an unbranched or branched aliphatic, cycloaliphatic or aromatic residue or a combination of these residues with 1 to 50 carbon atoms, in which at least one carbon atom is replaced by SiGG', SiG or Si and one or more carbon atoms can be replaced by O, O(C=O) or (C=O), G and G' represent, independently of one another, an unbranched or branched aliphatic or aromatic residue or a combination of these residues with 1 to 8 carbon atoms, n and m represent, independently of one another, 1, 2, 3 or 4 and m+n amount to 2 to 6, and in which the molar mass of the epoxide or the average molar mass of the mixture of epoxides is 360 to 2 500 g/mol.

Those epoxides of the component (a) are particularly preferred which exhibit one of the following constituents D, which in each case is bonded to the constituents A and A' via the silicon atom:

i. Si ii. SiG iii. SiGG' in which G and G' represent, independently of one another, an unbranched or branched aliphatic, cycloaliphatic or aromatic residue with 1 to 8 carbon atoms or a combination of these residues, in which one or more carbon atoms can be replaced by O, O(C=O), (C=O) or Si.

iv.

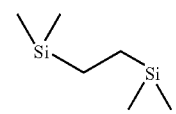

v.

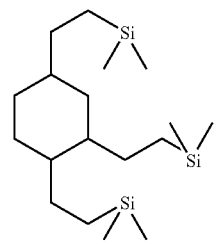

vi.

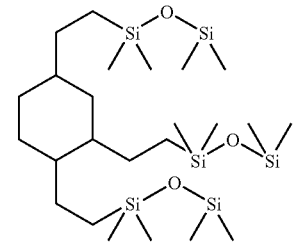

vii.

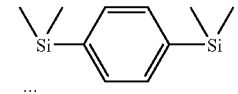

viii.

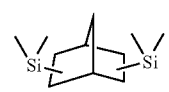

-continued ix.

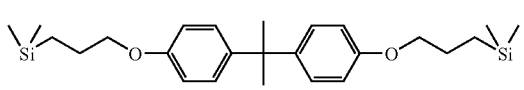

x.

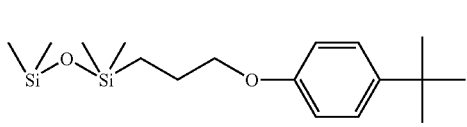

xi.

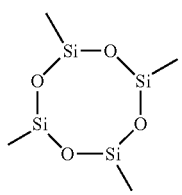

xii.

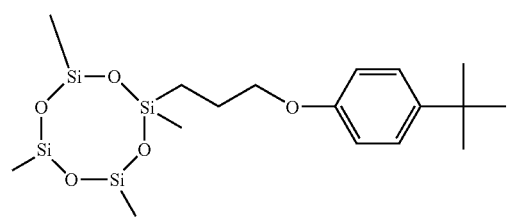

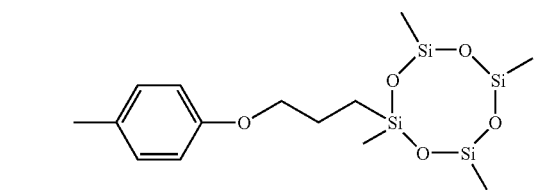

xiii.

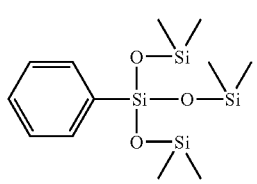

Preference is given, among the components (a), to those which exhibit Z=0 and in which G or G' represents a methyl group.

Particularly good results are achieved, for example but without limitation, with preparations comprising one or more of the following epoxides:

i. Silane, 1,2-ethylene-[1,2-dimethyl-1-[3-(oxiranyl-methoxy)propyl]-2-[2-(7-oxabicyclo[4.1.0]hept-3-yl)ethyl]-

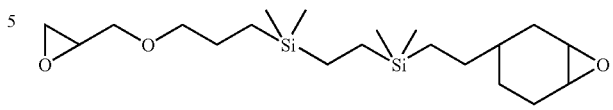

ii. Silane, 1,1',1''-(1,2,4-cyclohexylene-1-(dimethyl-[3-(oxiranylmethoxy)propyl])-2,4-bis[2-(7-oxabicyclo[4.1.0]hept-3-yl)ethyl])-

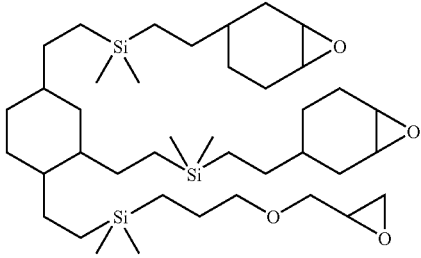

iii. Disiloxane, 1,1',1''-(1,2,4-cyclohexanetriyltri-2,1-ethanediyl)-1,1,3,3-tetramethyl-3-(oxiranyl-methoxy)propylbis[1,1,3,3-tetramethyl-2-(7-oxabicyclo[4.1.0]hept-3-yl)ethyl]-

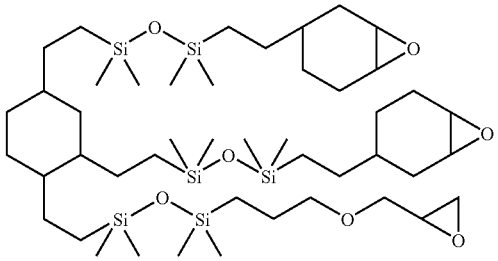

iv. Silane, 1,4-phenylenebis[dimethyl-1-[3-(oxiranyl-methoxy)propyl-4-[2-(7-oxabicyclo[4.1.0]hept-3-yl)ethyl]-

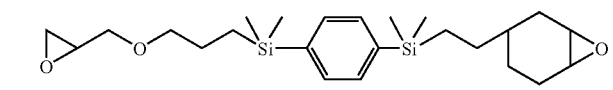

v. Silane, 2,5-bicyclo[2.2.1.]heptylenebis[dimethyl-2-[3-(oxiranylmethoxy)propyl]-5-[2-(7-oxabicyclo-[4.1.0]hept-3-yl)ethyl]-

vi. Silane, 1,1'-[bis(4,4'-hydroxyphenyl-2,2-propane-3,1-propanediyl)]-1-dimethyl[3-(oxiranylmethoxy)-propyl]-1'-dimethyl[2-(7-oxabicyclo[4.1.0]hept-3-yl)ethyl]-

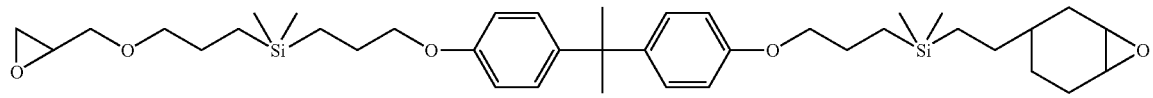

vii. Siloxane, 1,1'-[bis(4,4'-hydroxyphenyl-2,2-propane-3,1-propanediyl)-1,1,3,3-tetramethyl-1-[3-(oxiranylbutyl]-1'-[2-(7-oxabicyclo[4.1.0]hept-3-yl)ethyl]-

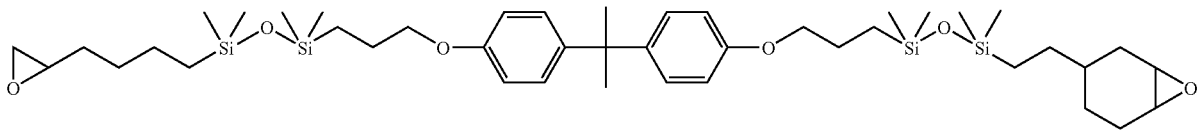

viii. Cyclotetrasiloxane, 2,4,6,8-tetramethyl-2,4,6-tris[2-(7-oxabicyclo[4.1.0]hept-3-yl)ethyl]-8-[3-(oxiranyl-methoxy)propyl]-

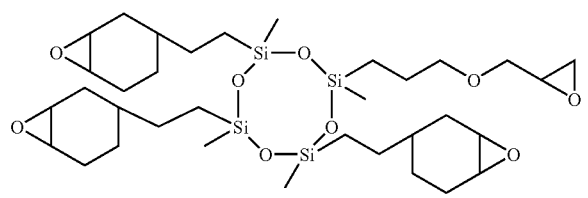

ix. Cyclotetrasiloxane, 2,4,6,8-tetramethyl-2,4,6-tris[2-(7-oxabicyclo[4.1.0]hept-3-yl)ethyl]-8-[4-oxiranylbutyl]-

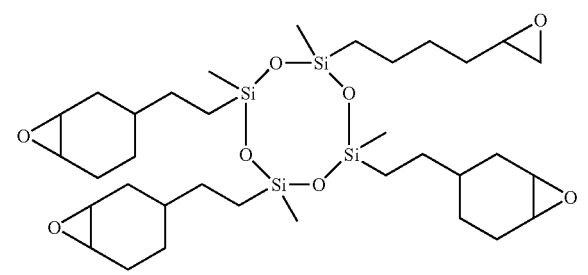

x. Cyclotetrasiloxane, 1,1'-[bis(4,4'-hydroxyphenyl-2,2-propane-3,1-propanediyl)]bis[2,4,6,8-tetramethyl-4,6-bis[3-(oxiranylmethoxy)propyl]-8-[2-(7-oxabicyclo[4.1.0]hept-3-yl)ethyl]-

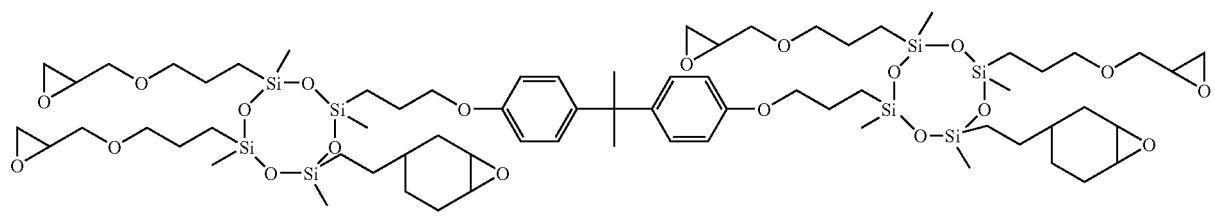

xi. Trisiloxane, 3-[[dimethyl-[2-(7-oxabicyclo-[4.1.0]hept-3-yl)ethyl]silyl]oxy]-1,1,5,5-tetramethyl-1-[2-(7-oxabicyclo[4.1.0]hept-3-yl)ethyl]-5-(oxiranylmethoxy)propyl]-3-phenyl-

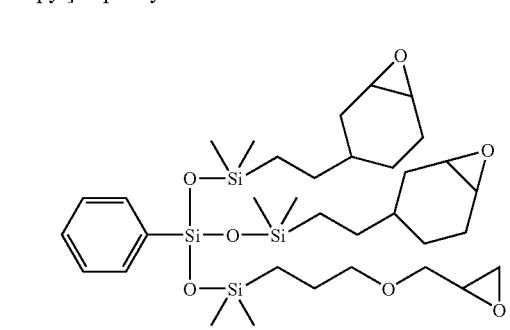

xii. Trisiloxane, 3-[[dimethyl-[2-(7-oxabicyclo-[4.1.0]hept-3-yl)ethyl]silyl]oxy]-1,1,5,5-tetramethyl-1-[2-(7-oxabicyclo[4.1.0]hept-3-yl)ethyl]-5-[2-(oxiranylethyl)]-3-phenyl-

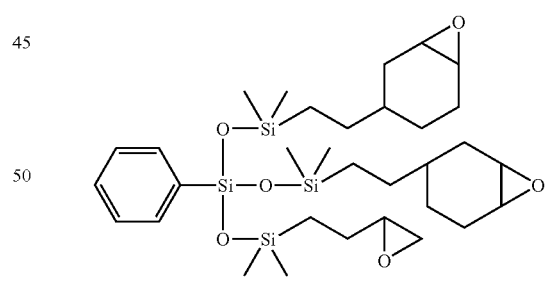

The polymerizable preparations according to the invention can, in addition to the silicon-comprising epoxides described, comprise other epoxides as component (b). For example, the epoxides disclosed in U.S. Pat. Nos. 2,716,123, 2,948,688, 2,948,688, 2,985,667, 2,750,395, 2,863,881 and 3,187,018 are included in their entirety as constituents in component (b) of the preparation according to the invention. The following examples are counted among them: 3,4-epoxycyclohexylmethyl 3,4-epoxycyclohexanecarboxylate (U.S. Pat. No. 2,716,123), 3,4-epoxy-6-methylcyclohexyl 3,4-epoxy-6-methylcyclohexane-carboxylate (U.S. Pat. No. 2,716,123) or related epoxides, vinylcyclohexene diepoxide (U.S. Pat. No. 2,948,688), dicyclopentadiene dioxide (U.S. Pat. No. 2,985,667) or bis(3,4-epoxycyclohexylmethyl) adipate (U.S. Pat. Nos. 2,750,395, 2,863,881, 3,187,018).

Trisiloxane, 3-[[dimethyl[2-(7-oxabicyclo[4.1.0]hept-3-yl)ethyl]silyl]oxy]-1,1,5,5-tetramethyl-1,5-bis[2-(7-oxabi-cyclo[4.1.0]hept-3-yl)ethyl]-3-phenyl- (CAS number 90393-84-3), 7-oxabicyclo[4.1.0]heptane, 3,3',3'',3'''-[(2,4,6,8-tetramethylcyclotetrasiloxan-2,4,6,8-tetrayl)tetra-2,1-ethanediyl]tetrakis- (CAS number 121225-98-7), with the following formula:

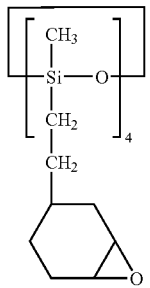

7-oxabicyclo[4.1.0]heptane, 3,3',3'',3''',3''''-[(2,4,6,8,10-pentamethylcyclopentasiloxan-2,4,6,8,10-pentayl)penta-2,1-ethanediyl]pentakis- (CAS number 141446-51-7), with the following formula:

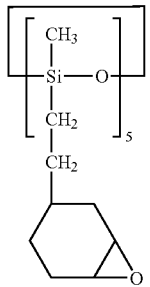

are likewise included.

The polyfunctional epoxides disclosed in WO 98/22521 can also be used as component (b) in the polymerizable materials.

The epoxides according to component (b) can exist in a concentration of 0 to 80 weight %, preferably 0 to 60 weight %, in each case with reference to the total weight of the preparation.

Inorganic fillers according to component (c) can be conventional dental fillers, for example quartz, ground, optionally X-ray-opaque, optionally reactive, glasses, difficultly soluble fluorides, such as $CaF_2$ or $YF_3$ (EP-B-0 238 025), silica gels and pyrogenic silica, and/or the granulates thereof.

Likewise, one or more water-soluble inorganic complex fluorides of the general formula $A_nMF_m$, in which A represents a mono- or polyvalent cation, M represents a metal from the III, IV or V main or subgroup, n represents an integer from 1 to 3 and m represents an integer from 4 to 6 (DE-A-4 445 266), can be present as fluoride-releasing constituents in the component (c) They can be present in a concentration of 3 to 85 weight %, preferably of 5 to 85 weight % and in particular of 30 to 85 weight %, with reference to the total weight, in the polymerizable preparations.

To improve the incorporation in the polymer matrix, it may be advantageous to render the fillers mentioned hydrophobic using conventional processes. Conventional hydrophobing agents are silanes, for example (3-glycidoxypropyl)trimethoxysilane, 5,6-epoxyhexyl-triethoxysilane or 2-(3,4-epoxycyclohexyl)ethyl-trimethoxysilane. The mean particle size of the inorganic fillers is preferably <20 µm, in particular <12 µm. Fillers with a mean particle size <7 µm are very particularly preferably used.

Cristobalite, calcium silicate, zirconium silicate, montmorillonites, such as bentonites, zeolites, including molecular sieves, such as sodium aluminum silicate, metal oxide powders, such as aluminum oxides or zinc oxides or their mixed oxides, barium sulfate, calcium carbonate, gypsum and plastic powders may also be suitable as fillers.

Initiators according to component (d) of the preparations according to the invention can be: Lewis or Brönsted acids or compounds which release such acids, which initiate the polymerization, for example $BF_3$ or its ether adducts ($BF_3$.THF, $BF_3$.$Et_2O$, and the like), $AlCl_3$, $FeCl_3$, $HPF_6$, $HAsF_6$, $HSbF_6$ or $HBF_4$, or substances which trigger the polymerization after irradiating with UV radiation or visible light, heat and/or pressure, such as, e.g., (ε-6-cumene)(ε-5-cyclopentadienyl)iron hexafluorophosphate, (ε-6-cumene)(ε-5-cyclopentadienyl)iron tetrafluoroborate, (ε-6-cumene) (ε-5-cyclopentadienyl) iron hexafluoro-antimonate, substituted diaryliodonium salts, triarylsulfonium salts and pyridinium salts. Peroxy compounds of the perester, diacyl peroxide, peroxydicarbonate and hydroperoxide type, for example, can be used as accelerators. Hydroperoxides are preferably used and particularly preferably, as accelerator, cumene hydroperoxide in approximately 70 to 90% solution in cumene is used. The ratio of photoinitiator to cumene hydroperoxide can be varied within wide limits from 1:0.001 to 1:10; however, a ratio from 1:0.1 to 1:6 is preferably used and particularly preferably from 1:0.5 to 1:4. The use of complexing agents, such as, for example, oxalic acid, 8-hydroxyquinoline, ethylenediaminetetraacetic acid and aromatic polyhydroxy compounds, is likewise possible.

Initiator systems consisting of different components can likewise be used, as are disclosed in EP 0 897 710 A2, WO 98/47046 or WO 98/47047. Initiator systems consisting of 1,2-diketones (such as camphorquinone), iodonium salts with anions which are not very coordinating (such as tolylcumyliodonium tetrakis(pentafluorophenyl)borate or tolylcumyliodonium tetrakis(3,5-bis(trifluoromethyl)phenyl)borate), together with tertiary aromatic amines (such as 2-butoxyethyl 4-(dimethylamino)benzoate or ethyl 4-(dimethylamino)benzoate), and/or suitable polyaromatics (such as anthracene) are preferably used.

Bases, such as, for example, tertiary amines, can be added as retarders.

The component (d) is present in the preparations according to the invention in an amount of 0.01 to 25 weight %, preferably 0.01 to 20 weight %, with reference to the total weight of the preparation.

Suitable auxiliaries according to component (e) can, for example, be stabilizers (e.g. tinuvins from Ciba), pigments or diluents conventionally used in the dental field.

It has surprisingly been found that the preparations according to the invention with the silicon-comprising epoxides according to component (a) exhibit, with advantageously low viscosity, just as good mechanical properties in the polymerized state as known dental materials.

Furthermore, it has been found surprisingly that the silicon-comprising epoxides or mixtures according to component (a) of the preparations according to the invention have, in spite of high reactivity, an excellent storage stability.

The epoxide-comprising polymerizable preparations according to the invention are suitable in particular as materials for dental purposes, for example for the preparation of plastic teeth or temporary filling materials, as coating agents, for the cementing of substrates, and as dental filling materials. Coating of plastics, glass, paper, films, metals or inorganic substrates is also possible, for example. Furthermore, plastics, glass, paper, films, metals or inorganic substrates, for example, can be cemented. In the process, the cementing can be carried out cold, hot or by irradiation or by chemical initiation.

The polymerizable preparation may be made available as a single-component system. Formulation as a two- or multicomponent system is likewise conceivable. In the course of this, one or more base pastes (A) can comprise epoxides or mixtures of epoxides of the components (a) and (b), a portion or the total amount of the fillers of the component (c), optionally retarders and/or accelerators according to component (d) and optionally auxiliaries of the component (e). One or more catalyst pastes (B), spatially separated therefrom, can exhibit one or more initiators according to component (d), optionally retarders and/or accelerators according to component (d), optionally a portion of the fillers of the component (c) and optionally auxiliaries according to component (e). The pastes (A) and (B) are then reacted with one another to obtain the polymerizable preparation. This takes place, for example, through automatic or manual mixing of base and catalyst pastes.

The preparation according to the invention can be packaged in various containers. Suitable containers are, e.g., cartridges with one or more compartments, mixing capsules or tubes, including screw-cap tubes. Furthermore, the polymerizable preparation can be present in various dispensing devices.

Examples of monomer compositions which achieve the object of the present invention are mentioned in the following table. The bending strength and the compressive strengths were determined according to ISO 4049. The volume shrinkage was calculated from the densities and volumes, determined according to Archimedes' principle, of the unpolymerized and of the polymerized preparations.

The monomers or monomer mixtures according to component (a) all exhibited a viscosity of less than 8 Pa·s. The viscosity was determined in a force-controlled manner and the epoxides or the epoxide mixtures according to component (a) were found to be Newtonian fluids in the measurement range from 5–500 Pa.

Monomer compositions

| | Amounts in weight % | | | | | |
|---|---|---|---|---|---|---|
| | Monomer composition 1 | Monomer composition 2 | Monomer composition 3 | Monomer composition 4 | Monomer composition 5 | Monomer composition 6 |
| 7-Oxabicyclo[4.1.0]heptane, 3,3',3'',3'''-[(2,4,6,8-tetramethylcyclotetrasiloxan-2,4,6,8-tetrayl)tetra-2,1-ethanediyl]-tetrakis- | 50 | 50 | 67 | 33 | 67 | |
| Silane, 1,4-phenylenebis-[dimethyl-1-[3-(oxiranylmethoxy)propyl-4-[2-(7-oxabicyclo[4.1.0]hept-3-yl)ethyl]- | 50 | 35 | 33 | 34 | | |
| 2,5-bicyclo[2.2.1.]heptylenebis-[dimethyl-2-[3-(oxiranylmethoxy)propyl]-5-[2,7-oxabicyclo[4.1.0]hept-3-yl)ethyl]- | | | | | 33 | 33 |
| Cyclotetrasiloxane, 2,4,6,8-tetramethyl-2,4,6-tris[2-(7-oxabicyclo[4.1.0]hept-3-yl)ethyl]-8-[3-(oxiranylmethoxy)propyl]- | | | | 33 | | |
| Trisiloxane, 3-[[dimethyl-[2-(7-oxabicyclo[4.1.0]hept-3-yl)-ethyl]silyl]oxy]-1,1,5,5-tetramethyl-1-[2-(7-oxabicyclo-[4.1.0]hept-3-yl)ethyl]-5-(oxiranylmethoxy)propyl]-3-phenyl- | | 15 | | | | 67 |

Compositions according to the invention with initiators and fillers, and their bending strength, water uptake and volume shrinkage

| | Amounts in weight % | | | | | | |
|---|---|---|---|---|---|---|---|
| | Example 1 | Example 2 | Example 3 | Example 4 | Example 5 | Example 6 | Example 7 |
| Monomer composition 1 | 20.6 | | | | | | |
| Monomer composition 2 | | 26.4 | | | | | |
| Monomer composition 3 | | | 32.2 | 29.9 | | | |
| Monomer composition 4 | | | | | 22.0 | | |
| Monomer composition 5 | | | | | | 27.9 | |
| Monomer composition 6 | | | | | | | 23.3 |
| Tolylcumyliodonium tetrakis-(pentafluorophenyl) borate | 2.0 | 2.1 | 2.0 | 2.2 | 2.1 | 2.1 | 2.2 |
| 2-Butoxyethyl 4-(dimethylamino)-benzoate | 0.3 | 0.2 | 0.3 | 0.3 | 0.3 | 0.2 | 0.3 |
| Camphorquinone | 0.6 | 0.5 | 0.5 | 0.6 | 0.6 | 0.5 | 0.6 |
| Quartz | 76.5 | 70.8 | 65.0 | | 75.0 | | 73.6 |
| Schott Glass GM 27884 | | | | 67.0 | | 69.3 | |
| Bending strength (ISO 4049) [MPa] | 107 | 95 | 98 | 89 | 115 | 108 | 92 |
| Compressive strength [MPa] | 354 | 378 | 349 | 332 | 394 | 403 | 320 |
| Volume shrinkage [vol %] | 1.3 | 1.8 | 1.7 | 1.7 | 1.4 | 1.3 | 1.9 |

What is claimed is:

1. A polymerizable preparation comprising:
   (a) 1 to 80 weight % of an epoxide or a mixture of epoxides of the general formula:

in which

A and A' represent, independently of one another, an unbranched or branched aliphatic, cycloaliphatic or aromatic residue or a combination of these residues with 0 to 16 carbon atoms, in which one or more carbon atoms can be replaced by O, O(C=O), C=O, Si, N or S, X represents an unbranched or branched aliphatic or aromatic residue or a combination of these residues with 3 to 16 carbon atoms, in which one or more carbon atoms can be replaced by O, O(C=O), (C=O), Si, N or S and an aliphatic terminal or centrally located epoxide group is present, L represents an unbranched or branched aliphatic, cycloaliphatic or aromatic residue or a combination of these residues with 6 to 30 carbon atoms, in which one or more carbon atoms can be replaced by O, O(C=O), (C=O), Si, N or S and a cycloaliphatic epoxide group is present, Z and Z' represent, independently of one another, H or an unbranched or branched aliphatic, cycloaliphatic or aromatic residue or a combination of these residues with 0 to 10 carbon atoms, in which one or more carbon atoms can be replaced by O, O(C=O), (C=O), Si, N or S, D represents one of the following constituents, which is bonded to the constituents A and/or A' via the silicon atom:

i. Si ii. SiG iii.

iv.

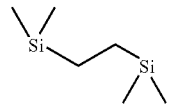

v.

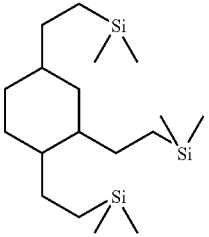

vi.

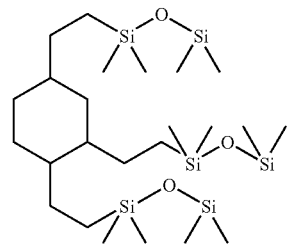

vii.

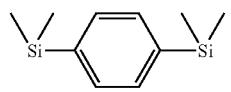

viii.
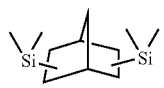

ix.
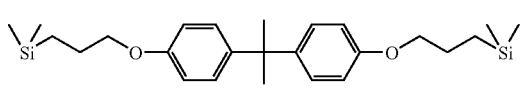

x.
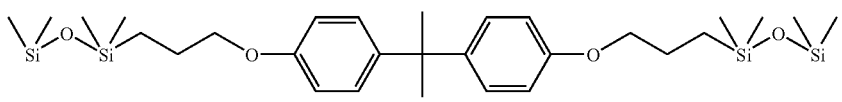

xi.
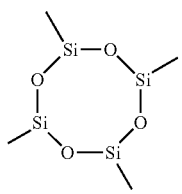

xii.
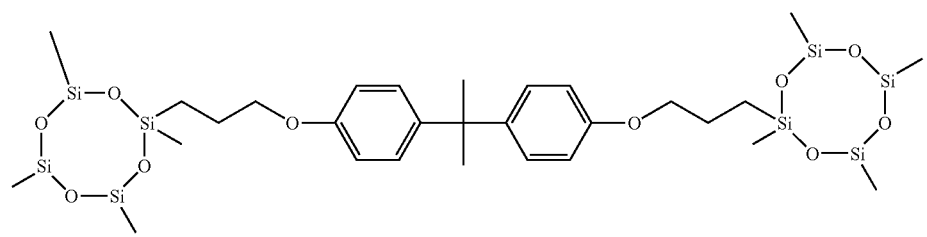

xiii.
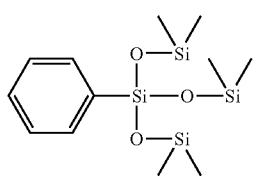

in which G and G' represent, independently of one another, an unbranched or branched aliphatic, cycloaliphatic or aromatic residue or a combination of these residues with 1 to 8 carbon atoms, in which one or more carbon atoms can be replaced by O, O(C=O), (C=O) or Si, n and m represent, independently of one another, 1, 2, 3 or 4, in which the molar mass of the epoxide or the average molar mass of the mixture of epoxides is 360 to 3,000 g/mol, (b) 0 to 80 weight % of an epoxide or a mixture of epoxides which are different from (a), (c) 3 to 85 weight % of fillers, (d) 0.01 to 25 weight % of initiators, retarders and/or accelerators, (e) 0 to 25 weight % of auxiliaries, in which the percentages are in each case with reference to the total weight of the preparation.

2. The polymerizable preparation as claimed in claim 1, comprising:

(a) 3 to 50 weight % of an epoxide or a mixture of epoxides of the general formula:

in which

A and A' represent, independently of one another, an unbranched or branched aliphatic, cycloaliphatic or aromatic residue or a combination of these residues with 0 to 12 carbon atoms, in which one or more carbon atoms can be replaced by O, O(C=O), C=O, Si, N or S, X represents an unbranched or branched aliphatic or aromatic residue or a combination of these residues with 3 to 14 carbon atoms, in which one or more carbon atoms can be replaced by O, O(C=O), (C=O), Si, N or S and and an aliphatic terminal or centrally located epoxide group is present, L represents an unbranched or branched aliphatic, cycloaliphatic or aromatic residue or a combination of these residues with 6 to 20 carbon atoms, in which one or more carbon atoms can be replaced by O, O(C=O), (C=O), Si, N or S and a cycloaliphatic epoxide group is present, Z and Z' represent, independently of one another, H or an unbranched or branched aliphatic, cycloaliphatic or aromatic residue or a combination of these residues with 0 to 10 carbon atoms, in which one or more carbon atoms can be replaced by O, O(C=O), (C=O) or Si, in which the molar mass of the epoxide or the average molar mass of the mixture of epoxides is 360 to 2,500 g/mol, (b) 0 to 60 weight % of an epoxide or a mixture of epoxides which are different from (a), (c) 15 to 85 weight % of fillers, (d) 0.01 to 20 weight % of initiators, retarders and/or accelerators, (e) 0 to 25 weight % of auxiliaries, in which the percentages are in each case with reference to the total weight of the preparation.

3. The polymerizable preparation as claimed in claim 1, comprising, as component (a), one or more of the following epoxides:

in which

A and A' represent, independently of one another, an unbranched or branched aliphatic, cycloaliphatic or aromatic residue or a combination of these residues with 0 to 12 carbon atoms, in which one or more carbon atoms can be replaced by O, O(C=O), C=O, Si, N or S, X represents an unbranched or branched aliphatic residue or a combination of these residues with 3 to 14 carbon atoms, in which one or more carbon atoms can be replaced by O, O(C=O), (C=O), Si, N or S and at least one tenninal aliphatic epoxide group is present, L represents an unbranched or branched aliphatic or cycloaliphatic residue or a combination of these residues with 7 to 15 carbon atoms, in which one or more carbon atoms can be replaced by O, O(C=O), (C=O), Si, N or S and a cycloaliphatic epoxide group of the following formula is present,

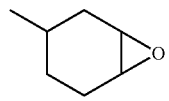

in which the molar mass of the epoxide or the average molar mass of the mixture of epoxides is 360 to 2,500 g/mol.

4. The polymerizable preparation as claimed in claim 1, comprising, as component (a), one or more of the following epoxides:

in which

A and A' represent, independently of one another, an unbranched or branched aliphatic, cycloaliphatic or aromatic residue or a combination of these residues with 0 to 10 carbon atoms, in which one or more carbon atoms can be replaced by O, O(C=O), C=O or Si, X represents a branched or unbranched aliphatic residue with 3 to 14 carbon atoms, in which one or more carbon atoms can be replaced by O, O(C=O), (C=O) or Si and at least one terminal aliphatic epoxide group is present, L represents an unbranched or branched aliphatic or cycloaliphatic residue or a combination of these residues with 7 to 15 carbon atoms, in which one or more carbon atoms can be replaced by O, O(C=O), (C=O) or Si and a cycloaliphatic epoxide group of the following formula is present,

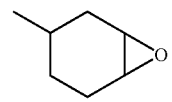

n and m represent, independently of one another, 1,2, 3 or 4 and m+n amount to 2 to 6, in which the molar mass of the epoxide or the average molar mass of the mixture of epoxides is 360 to 2,500 g/mol.

5. The polymerizable preparation as claimed in claim 1, comprising, as fillers according to component (c), quartz, ground glasses, silica gels and/or silicas, granulates thereof and/or ground plastics.

6. The polymerizable preparation as claimed in claim 1, comprising, as initiators, Lewis acids and/or Brönsted acids or compounds from which such acids arise by irradiation with UV light or visible light, pressure and/or heat or by chemical reaction.

7. The polymerizable preparation as claimed in claim 1 comprising, as accelerators, hydroxyl-functionalized epoxides.

8. The polymerizable preparation as claimed in claim 1, comprising, as auxiliaries, diluents, stabilizers, inhibitors and/or pigments.

9. The polymerizable preparation as claimed in claim 1, comprising at least one base paste, comprising epoxides or mixtures of epoxides of the components (a) and (b), a portion or the total amount of the fillers of the component (c), optionally retarders and/or accelerators according to component (d), and optionally auxiliaries of the component (e), and, spatially separated therefrom, at least one catalyst paste, comprising at least one initiator according to component (d), optionally a portion of the fillers of the component (c) and optionally auxiliaries according to component (e), in which base and catalyst paste are mixed with one another to obtain the polymerizable preparation.

10. A cement comprising the polymerizable preparation as claimed in claim 1.

11. A container comprising a polymerizable preparation as claimed in claim 1.

12. A dispensing device, comprising a polymerizable preparation as claimed in claim 1.

13. The container of claim 11 wherein the container is a cartridge.

14. The container of claim 11 wherein the container is a mixing capsule.

15. A method of coating a substrate comprising applying the polymerizable preparation as claimed in claim 1 to the substrate.

16. A method of cementing at least two substrates, the method comprising applying the polymerizable preparation as claimed in claim 1 to at least one substrate and contacting the at least two substrates together to cement them together.

17. The polymerizable preparation as claimed in claim 1 comprising, as component (a), one or more of the following epoxides:

i. Silane, 1,2-ethylene-[1,2-dimethyl-1-[3-(oxiranyl-methoxy)propyl]-2-[2-(7-oxabicyclo[4.1.0]hept-3-yl)ethyl]-

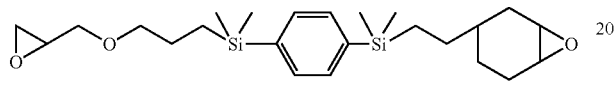

ii. Silane, 1,1'1",-(1,2,4-cyclohexylene-1-(dimethyl[3-(oxiranylmethoxy)propyl])-2,4-bis[2-(7-oxabicyclo[4.1.0]hept-3-yl)ethyl])-

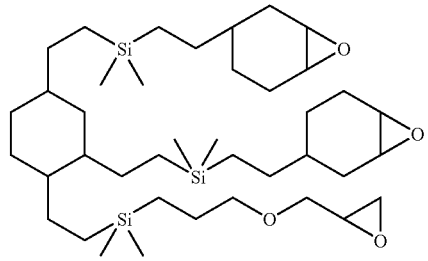

iii. Disiloxane, 1,1',1",-(1,2,4-cyclohexanetriyltri-2,1-ethanediyl)-1,1,3,3-tetramethyl-3-(oxiranylmethoxy)propylbis[1,1,3,3-tetramethyl-2-(7-oxabicyclo[4.1.0]hept-3-yl)ethyl]-

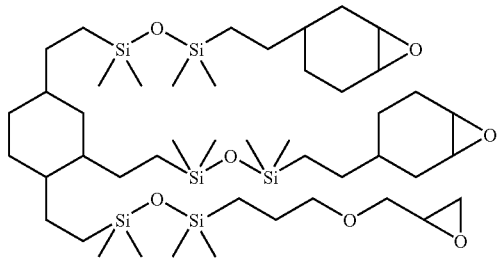

iv. Silane, 2,5-bicyclo[2.2.1]heptylenebis[dimethyl-2-[3-(oxiranylmethoxy)propyl]-5-[2-(7-oxabicyclo[4.1.0]hept-3-yl)ethyl]-

v. Silane, 1,1'-[bis(4,4'-hydroxyphenyl-2,2-propane-3,1-propanediyl)]-1-dimethyl[3-(oxiranylmethoxy)propyl]-1'-dimethyl [2-(7-oxabicyclo[4.1.0]hept-3-yl)ethyl]-

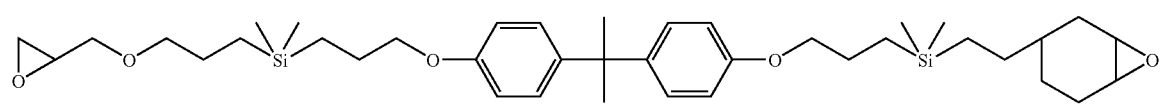

vi. Siloxane, 1,1'-[bis(4,4'-hydroxyphenyl-2,2-propane-3,1-propanediyl)-1,1,3,3-tetramethyl]-1-[3-(oxiranylbutyl]-1'-[2-(7-oxabicyclo[4.1.0]hept-3-yl)ethyl]-

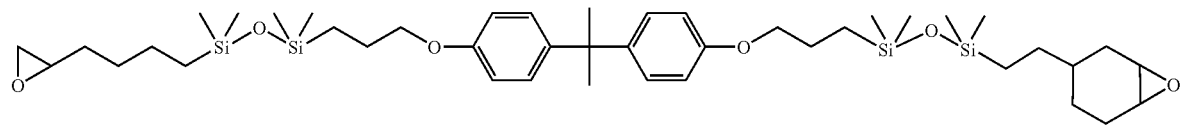

vii. Cyclotetrasiloxane, 2,4,6,8-tetramethyl-2,4,6-tris[2-(7-oxabicyclo[4.1.0]hept-3-yl)ethyl]-8-[3-(oxiranylmethoxy)propyl]-

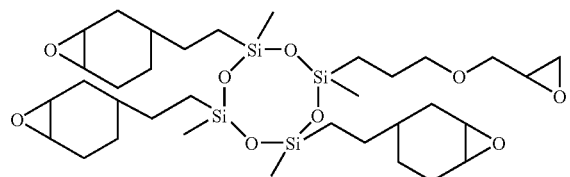

viii. Cyclotetrasiloxane, 2,4,6,8-tetramethyl-2,4,6-tris[2-(7-oxabicyclo [4.1.0]hept-3-yl)ethyl]-8-[4-oxiranylbutyl]-

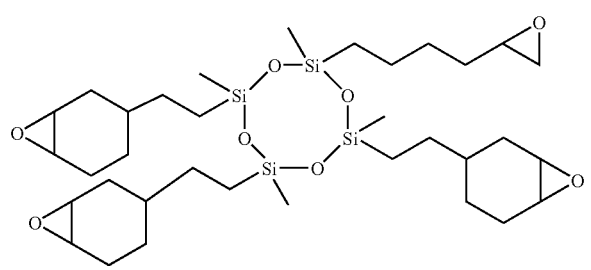

ix. Cyclotetrasiloxane, 1,1'-[bis(4,4'-hydroxyphenyl-2,2-propane-3,1-propanediyl)]-bis[2,4,6,8tetramethyl4,6-bis[3-(oxiranylmethoxy)propyl]-8-[2(7oxabicyclo [4.1.0]hept-3-yl)ethyl]-

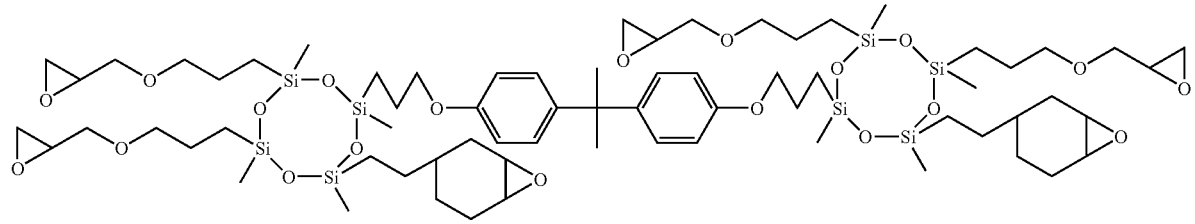

x. Trisiloxane, 3-[[dimethyl-[2-(7-oxabicyclo[4.1.0]hept-3-yl)ethyl]silyl]oxy]-1,1,5,5-tetramethyl-1-[2-(7-oxabicyclo[4.1.0]hept-3-yl)ethyl]-5-(oxiranylmethoxy)propyl]-3-phenyl-

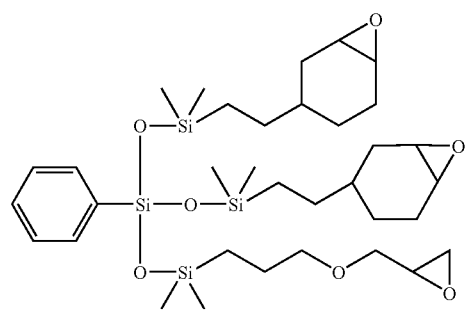

xi. Trisiloxane, 3[-[dimethyl-[2-(7-oxabicyclo[4.1.0]hept-3-yl)ethyl]silyl]oxy]-1,1,5,5-tetramethyl-1-[2-(7-oxabicyclo[4.1.0]hept-3-yl)ethyl]-5-[2-(oxiranylethyl)]-3-phenyl-

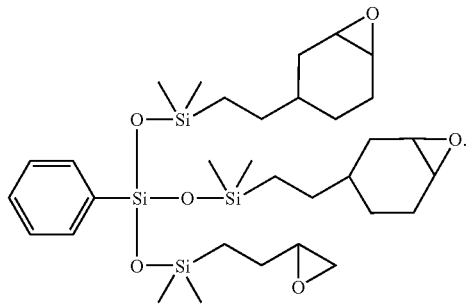

18. A dental material comprising the polymerizable preparation as claimed in claim 1.

19. A polymerizable preparation comprising:
(a) 1 to 80 weight % of one or more of the following epoxides:
    i. Silane, 1,2-ethylene-[1,2-dimethyl-1-[3-(oxiranylmethoxy)propyl]-2-[2-(7-oxabicyclo[4.1.0]hept-3-yl)ethyl]-

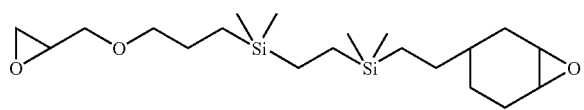

ii. Silane, 1,1',1"-(1,2,4-cyclohexylene-1-(dimethyl[3-(oxiranylmethoxy)propyl])-2,4-bis[2-(7-oxabicyclo [4.1.0]hept-3-yl)ethyl])-

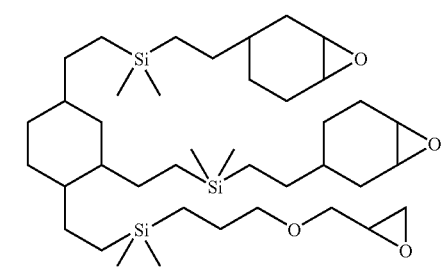

iii. Disiloxane, 1,1',1'',-(1,2,4-cyclohexanetriyltri-2,1-ethanediyl)-1,1,3,3-tetramethyl-3-(oxiranylmethoxy)propylbis[1,1,3,3-tetramethyl-2-(7-oxabicyclo[4.1.0]hept-3-yl)ethyl]-

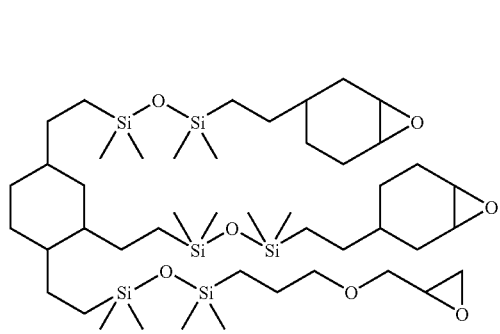

iv. Silane, 2,5-bicyclo[2.2.1]heptylenebis[dimethyl-2-[3-(oxiranylmethoxy)propyl]-5-[2-(7-oxabicyclo[4.1.0]hept-3-yl)ethyl]-

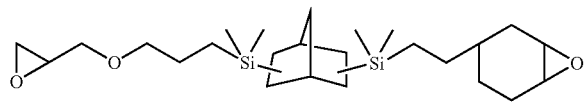

v. Silane, 1,1'-[bis(4,4'-hydroxyphenyl-2,2-propane-3,1-propanediyl)]-1-dimethyl[3-(oxiranylmethoxy)propyl]-1'-dimethyl[2-(7-oxabicyclo[4.1.0]hept-3-yl)ethyl]-

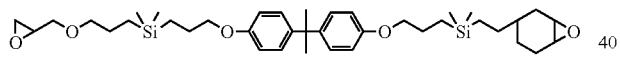

vi. Siloxane, 1,1'-[bis(4,4'-hydroxyphenyl-2,2-propane-3,1-propanediyl)-1,1,3,3-tetramethyl]-1-[3-(oxiranylbutyl]-1'-[2-(7-oxabicyclo[4.1.0]hept-3-yl)ethyl]-

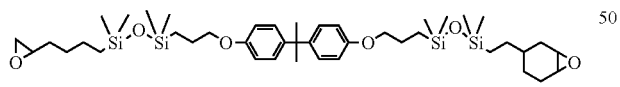

vii. Cyclotetrasiloxane, 2,4,6,8-tetramethyl-2,4,6-tris[2-(7-oxabicyclo[4.1.0]hept-3-yl)ethyl]-8-[3-(oxiranylmethoxy)propyl]-

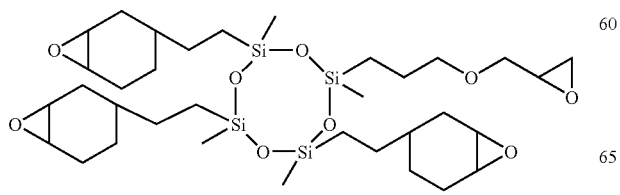

viii. Cyclotetrasiloxane, 2,4,6,8-tetramethyl-2,4,6-tris[2-(7-oxabicyclo[4.1.0]hept-3-yl)ethyl]-8-[4-oxiranylbutyl]-

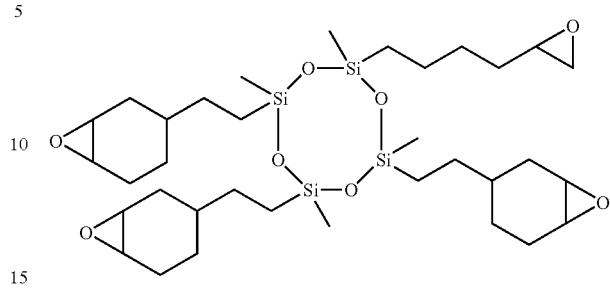

ix. Cyclotetrasiloxane, 1,1'-[bis(4,4'-hydroxyphenyl-2,2-propane-3,1-propanediyl)]bis[2,4,6,8-tetramethyl-4,6-bis[3-(oxiranylmethoxy)propyl]-8-[2-7-oxabicyclo[4.1.0]hept-3-yl)ethyl]-

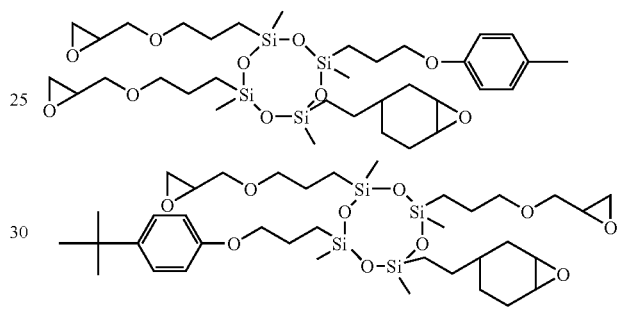

x. Trisiloxane, 3-[[dimethyl-[2-(7-oxabicyclo[4.1.0]hept-3-yl)ethyl]silyl]oxy]-1,1,5,5-tetramethyl-1-[2-(7-oxabicyclo[4.1.0]hept-3-yl)ethyl]-5-(oxiranylmethoxy)propyl]-3-phenyl-

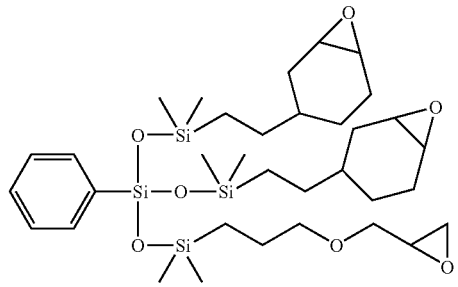

xi. Trisiloxane, 3-[[dimethyl-[2-(7-oxabicyclo[4.1.0]hept-3-yl)ethyl]silyl]oxy]-1,1,5,5-tetramethyl-1-[2-(7-oxabicyclo[4.1.0]hept-3-yl)ethyl]-5[2-(oxiranylethyl)]-3-phenyl-

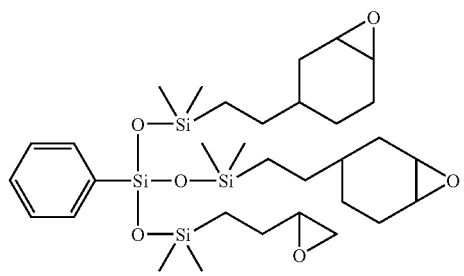

(b) 0 to 80 weight % of an epoxide or a mixture of epoxides which are different from (a), (c) 3 to 85 weight % of fillers, (d) 0.01 to 25 weight % of initiators, retarders and/or accelerators, (e) 0 to 25 weight % of auxiliaries, in which the percentages are in each case with reference to the total weight of the preparation.

20. The polymerizable preparation as claimed in claim 19, comprising:

(a) 3 to 50 weight % of the one or more epoxides, (b) 0 to 60 weight % of an epoxide or a mixture of epoxides which are different from (a), (c) 15 to 85 weight % of fillers, (d) 0.01 to 20 weight % of initiators, retarders and/or accelerators, (e) 0 to 25 weight % of auxiliaries, in which the percentages are in each case with reference to the total weight of the preparation.

21. The polymerizable preparation as claimed in claim 19, comprising, as fillers according to component (c), quartz, ground glasses, silica gels and/or silicas, granulates thereof and/or ground plastics.

22. The polymerizable preparation as claimed in claim 19, comprising, as initiators, Lewis acids and/or Brönsted acids or compounds from which such acids arise by irradiation with UV light or visible light, pressure and/or heat or by chemical reaction.

23. The polymerizable preparation as claimed in claim 19 comprising, as accelerators, hydroxy-functionalized epoxides.

24. The polymerizable preparation as claimed in claim 19, comprising, as auxiliaries, diluents, stabilizers, inhibitors and/or pigments.

25. The polymerizable preparation as claimed in claim 19, comprising at least one base paste, comprising epoxides or mixtures of epoxides of the components (a) and (b), a portion or the total amount of the fillers of the component (c), optionally retarders and/or accelerators according to component (d), and optionally auxiliaries, of the component (e), and, spatially separated therefrom, at least one catalyst paste, comprising at least one initiator according to component (d), optionally a portion of the fillers of the component (c) and optionally auxiliaries according to component (e), in which base and catalyst paste are mixed with one another to obtain the polymerizable preparation.

26. A cement comprising the polymerizable preparation as claimed in claim 19.

27. A dental material comprising the polymerizable preparation as claimed in claim 19.

28. A container comprising a polymerizable preparation as claimed in claim 19.

29. A dispensing device, comprising a polymerizable preparation as claimed in claim 19.

30. The container of claim 28 wherein the container is a cartridge.

31. The container of claim 28 wherein the container is a mixing capsule.

32. A method of coating a substrate comprising applying the polymerizable preparation as claimed in claim 19 to the substrate.

33. A method of cementing at least two substrates, the method comprising applying the polymerizable preparation as claimed in claim 19 to at least one substrate and contacting the at least two substrates together to cement them together.

* * * * *

UNITED STATES PATENT AND TRADEMARK OFFICE
CERTIFICATE OF CORRECTION

PATENT NO. : 7,235,602 B2
APPLICATION NO. : 10/468532
DATED : June 26, 2007
INVENTOR(S) : Klettke et al.

It is certified that error appears in the above-identified patent and that said Letters Patent is hereby corrected as shown below:

On the title page item (56), column 2, under Foreign Patent Documents, delete "DE 43 40 949 A1  9/1995" and insert --DE 43 40 949 A1  6/1995--;

On page 2, under Other Publications column 1, line 9, delete "vo." and insert --vol.--;

Signed and Sealed this

Twenty-fifth Day of March, 2008

JON W. DUDAS
*Director of the United States Patent and Trademark Office*